United States Patent
Haga

(10) Patent No.: US 8,974,733 B2
(45) Date of Patent: Mar. 10, 2015

(54) AUTOMATIC ANALYZER

(75) Inventor: Tadashi Haga, Shizuoka (JP)

(73) Assignee: Beckham Coulter, Inc., Brea, CA (US)

( * ) Notice: Subject to any disclaimer, the term of this patent is extended or adjusted under 35 U.S.C. 154(b) by 171 days.

(21) Appl. No.: 13/473,544

(22) Filed: May 16, 2012

(65) Prior Publication Data

US 2012/0270336 A1    Oct. 25, 2012

Related U.S. Application Data

(63) Continuation of application No. PCT/JP2010/006832, filed on Nov. 22, 2010.

(30) Foreign Application Priority Data

Nov. 26, 2009  (JP) .................................. 2009-269039

(51) Int. Cl.

| | | |
|---|---|---|
| G01N 21/17 | (2006.01) | |
| G01N 33/543 | (2006.01) | |
| G01N 35/02 | (2006.01) | |
| G01N 21/25 | (2006.01) | |
| G01N 35/00 | (2006.01) | |
| G01N 21/82 | (2006.01) | |
| G01N 21/27 | (2006.01) | |

(52) U.S. Cl.
CPC ........ *G01N 35/028* (2013.01); *G01N 2021/825* (2013.01); *G01N 21/272* (2013.01); *G01N 21/253* (2013.01); *G01N 35/00613* (2013.01)
USPC ................................ 422/73; 422/65; 436/164

(58) Field of Classification Search
CPC  G01N 2021/825;  G01N 21/17;  G01N 33/543
See application file for complete search history.

(56) References Cited

FOREIGN PATENT DOCUMENTS

| JP | 10-223379 A | 8/1998 |
|---|---|---|
| JP | 2005-102436 A | 4/2005 |
| JP | 2008-275473 A | 11/2008 |

OTHER PUBLICATIONS

The International Search Report, from PCT/JP2010/006832, mailed Feb. 1, 2011, 2 pages total (1 page in Japanese and 1 page with English Translation).

*Primary Examiner* — P. Kathryn Wright

(74) *Attorney, Agent, or Firm* — Kilpatrick Townsend & Stockton LLP

(57) ABSTRACT

Using a microplate having wells for the dispensing and reaction of a sample including blood and a reagent, an automatic analyzer captures an image of whether reactions have occurred inside the wells and performs analysis, the automatic analyzer comprising: a section for, with captured images obtained by capturing images of the inside of the wells corresponding to categories, calculating photometric parameters of the images, evaluating whether a measurement result based on the images is negative for each test, and analyzing characteristic information of the sample; a section for matching and storing characteristic information of samples and measurement results; a section for extracting a photometric parameter of a measurement result judged as negative; and a section for calculating a difference between maximum and minimum values of an extracted photometric parameter, determining whether a measurement is valid using the difference, and adding a result of the determination to characteristic information.

13 Claims, 7 Drawing Sheets

FIG. 2

| Result of ABO | Result of Reagent | | | |
|---|---|---|---|---|
| | Anti-A | Anti-B | Acell | Bcell |
| Type A | + | − | − | + |
| Type B | − | + | + | − |
| Type O | − | − | + | + |
| Type AB | + | + | − | − |

FIG. 3

| Result of 'Rho (D) | Result of Reagents | |
|---|---|---|
| | Ref | Anti-D |
| Rh(+) | − | + |
| Rh(−) | − | − |

| Reagent Name | Threshold Value for Qualitative Determination | | | | | |
|---|---|---|---|---|---|---|
| | SPC | | P/C | | LIA | |
| | Low | High | (+)limit | (−)limit | (+)limit | (−)limit |
| ref | 10 | 20 | 30 | 20 | 400 | 100 |
| Anti-D | 10 | 20 | 30 | 20 | 400 | 100 |
| Anti-A | 10 | 20 | 30 | 20 | 400 | 100 |
| Anti-B | 10 | 20 | 30 | 20 | 400 | 100 |

FIG. 6

| Reagent Name | Abnormal Dispensing (Fibrin Suction) | | | | Normal Dispensing | | | |
|---|---|---|---|---|---|---|---|---|
| | P/C | SPC | LIA | Result | P/C | SPC | LIA | Result |
| ref | 43 | 35 | 491 | − | 50 | 26 | 679 | − |
| Anti-D | 16 | 7 | 0 | + | 12 | 1 | 0 | + |
| Anti-A | 54 | 29 | 869 | − | 11 | 1 | 0 | + |
| Anti-B | 45 | 34 | 390 | − | 51 | 27 | 689 | − |
| Photometric Value Range | 11 | 6 | 479 | | 1 | 1 | 10 | |
| Test Result | Type O | | | | Type A | | | |
| | Rh(+) | | | | Rh(+) | | | |

FIG. 7

| | Abnormal | Normal | Threshold Value |
|---|---|---|---|
| P/C range | 11 | 1 | 5 |
| SPC range | 6 | 1 | 5 |
| LIA range | 479 | 10 | 100 |

AUTOMATIC ANALYZER

CROSS-REFERENCE TO RELATED APPLICATIONS

This application is a Continuation of International Application No. PCT/JP2010/006832, filed Nov. 22, 2010, which claims the benefit of priority to Japanese Application No. 2009-269039, filed Nov. 26, 2009, the disclosures of which are herein incorporated by reference.

TECHNICAL FIELD

The present invention relates to an automatic analyzer for performing an immunological agglutination reaction.

BACKGROUND ART

Conventionally, microplates have been used in analysis of components such as blood and body fluids, and each of such microplates consists of a plurality of reaction containers referred to as wells provided in a matrix. A sample containing a substance to be analyzed, and a reaction reagent containing a substance that causes an antigen-antibody reaction with the substance to be analyzed are dispensed into each well of the microplates. Then, after the passage of a predetermined period of time since the dispensing, whether or not an agglutination reaction has occurred in the well is captured by image capturing means such as a CCD camera, and the image data obtained by this image capturing is used to analyze the components of the sample.

In the analysis described above, a determination of being a negative or positive is made based on the captured-image data (captured image) obtained by capturing an image of a reactant, and contamination of a foreign substance largely influences the analysis result. In order to check reaction results accurately, it is important to perform analysis processing on a reactant free of foreign substances. In regards to such a demand, a checking method is disclosed for detecting the pressure in a dispensing tube by a pressure sensor, capturing an image of a container by a CCD camera, and checking a suction amount and a dispensing amount in order to prevent contamination of foreign substances from occurring (see, for example, Patent Literature 1).

Patent Literature 1: Japanese Laid-Open Publication No. 2000-193670

DISCLOSURE OF THE INVENTION

Technical Means

The present invention provides an automatic analyzer comprising: a dispensing section for dispensing a sample, including blood, and a reagent; a reaction section including a substrate having a plurality of reaction containers for allowing the sample including blood to react with the reagent therein; a photometry section for capturing an image of the inside of each of the reaction containers; an analysis section for analyzing the sample on the basis of whether or not reactions have occurred inside the reaction containers, wherein with a plurality of captured images obtained by capturing an image of the inside of the plurality of reaction containers corresponding to a plurality of categories of examination respectively, the analysis section calculates a photometric parameter of each of the images, and on the basis of the photometric parameter, and with a case where no reactions have occurred in the reaction containers being defined as negative, judges whether or not a measurement result based on the captured images is negative for each of tests, and analyzes characteristic information of the sample; a storage section for matching and storing the characteristic information of the sample and the measurement result; an extraction section for extracting the photometric parameter of the measurement result that is judged to be negative by the analysis section; and a determination processing section for calculating a difference between a maximum value and a minimum value of the photometric parameter extracted by the extraction section, determining whether or not the measurement result is valid using the calculated difference, and adding a result of the determination to the characteristic information of the corresponding sample.

Alternatively, in the present invention, in an automated analyzer, using a substrate having a plurality of reaction containers for dispensing a sample, including blood, and a reagent thereinto and allowing the sample to react with the reagent therein, for capturing an image of the inside of each of the reaction containers and analyzing the sample on the basis of whether or not reactions have occurred inside the reaction containers, comprised are: an analysis section, wherein with a plurality of captured images obtained by capturing an image of the inside of the plurality of reaction containers corresponding to a plurality of tests respectively, the analysis section calculates a photometric parameter of each of the images, and on the basis of the photometric parameter, and with a case where no reactions have occurred in the reaction containers being defined as negative, judges whether or not a measurement result based on the captured images is negative for each of the categories of examination, and analyzes characteristic information of the sample; a storage section for matching and storing the characteristic information of the sample and the measurement result; an extraction section for extracting the photometric parameter of the measurement result that is judged to be negative by the analysis section; and a determination processing section for calculating a difference between a maximum value and a minimum value of the photometric parameter extracted by the extraction section, determining whether or not the measurement result is valid using the calculated difference, and adding a result of the determination to the characteristic information of the corresponding sample.

In one embodiment, in the invention described above, and in the automatic analyzer according to the present invention, at least two of the photometric parameters are selected from the group consisting of P/C, SPC and LIA; and the determination processing section determines that the measurement result is invalid if the difference of at least one of the photometric parameters is outside a predetermined range.

In another embodiment, in the invention described above, and in the automatic analyzer according to the present invention, at least one of the photometric parameters is selected from the group consisting of P/C, SPC and LIA; and the determination processing section determines that the measurement result is invalid if the difference of all of the photometric parameters is outside a predetermined range.

In still another embodiment, in the invention described above, and in the automatic analyzer according to the present invention, one of reagents used in accordance with the plurality of tests is a reference reagent that always indicates negative.

In still another embodiment, in the invention described above, the automatic analyzer according to the present invention further comprises an output section for outputting information to the effect that the measurement result is invalid if the measurement result is determined to be invalid by the determination processing section.

In a different aspect, an automatic analyzing method, using a substrate having a plurality of reaction containers for allowing a sample, including blood, and a reagent to be dispensed and allowing the sample to react with the reagent therein, for capturing an image of the inside of each of the reaction containers and analyzing the sample on the basis of whether or not reactions have occurred inside the reaction containers, is provided. The method comprises: an analysis step of, with a plurality of captured images obtained by capturing an image of the inside of the plurality of reaction containers corresponding to a plurality of categories of examination respectively, calculating a photometric parameter of each of the images, and on the basis of the photometric parameter, and with a case where no reactions have occurred in the reaction containers being defined as negative, judging as to whether or not a measurement result based on the captured images is negative for each of tests, and analyzing characteristic information of the sample; a storing step of matching and storing the characteristic information of the sample and the measurement result; an extracting step of extracting the photometric parameter of the measurement result that is judged to be negative by the analysis section; and a determination processing step of calculating a difference between a maximum value and a minimum value of the photometric parameter extracted by the extraction section, determining whether or not the measurement result is valid using the calculated difference, and adding a result of the determination to characteristic information of the corresponding sample.

In various embodiments, the method according to the present invention comprises any one or more of the characteristics of the automatic analyzer according to the present invention.

In a different aspect, a control program used in an automatic analyzer, using a substrate having a plurality of reaction containers for allowing a sample, including blood, and a reagent to be dispensed and allowing the sample to react with the reagent therein, for capturing an image of the inside of each of the reaction containers and analyzing the sample on the basis of whether or not reactions have occurred inside the reaction containers, is provided. The control program is for implementing processing executed by the automatic analyzer in accordance with an instruction by an operator, the processing comprising: an analysis procedure of, with a plurality of captured images obtained by capturing an image of the inside of the plurality of reaction containers corresponding to a plurality of tests respectively, calculating a photometric parameter of each of the images, and on the basis of the photometric parameter, and with a case where no reactions have occurred in the reaction containers being defined as negative, judging as to whether or not a measurement result based on the captured images is negative for each of tests, and analyzing characteristic information of the sample; a storing procedure of matching and storing the characteristic information of the sample and the measurement result; an extracting procedure of extracting the photometric parameter of the measurement result that is judged to be negative by the analysis section; and a determination processing procedure of calculating a difference between a maximum value and a minimum value of the photometric parameter extracted by the extraction section, determining as to whether or not the measurement result is valid using the calculated difference, and adding a result of the determination to characteristic information of the corresponding sample.

In various embodiments, the program according to the present invention comprises any one or more of the characteristics of the automatic analyzer and method according to the present invention.

In a different aspect, a computer readable recording medium having a control program recorded thereon used in an automatic analyzer, using a substrate having a plurality of reaction containers for allowing a sample, including blood, and a reagent to be dispensed and allowing the sample to react with the reagent therein, for capturing an image of the inside of each of the reaction containers and analyzing the sample on the basis of whether or not reactions have occurred inside the reaction containers, is provided. The control program is for implementing processing executed by the automatic analyzer in accordance with an instruction by an operator, the processing comprising: an analysis procedure of, with a plurality of captured images obtained by capturing an image of the inside of the plurality of reaction containers corresponding to a plurality of tests respectively, calculating a photometric parameter of each of the images, and on the basis of the photometric parameter, and with a case where no reactions have occurred in the reaction containers being defined as negative, judging whether or not a measurement result based on the captured images is negative for each of tests, and analyzing characteristic information of the sample; a storing procedure of matching and storing the characteristic information of the sample and the measurement result; an extracting procedure of extracting the photometric parameter of the measurement result that is judged to be negative by the analysis section; and a determination processing procedure of calculating a difference between a maximum value and a minimum value of the photometric parameter extracted by the extraction section, determining whether or not the measurement result is valid using the calculated difference, and adding a result of the determination to characteristic information of the corresponding sample.

In various embodiments, the recording medium according to the present invention comprises anyone or more of the characteristics of the automatic analyzer, method and program according to the present invention.

Advantageous Effects of Invention

According to the present invention, a comparison between a threshold value and a difference between the maximum value and the minimum value of a photometric parameter obtained from captured-image data makes it possible to determine whether or not a measurement result is valid. This exerts an effect of obtaining a reliable measurement result.

BRIEF DESCRIPTION OF THE DRAWINGS

FIG. 2 is a table illustrating a combination of reagents being negative (−) and positive (+) in relation to the ABO blood group, according to the present embodiment of the present invention.

FIG. 3 is a table illustrating a combination of the Rho (D) blood group being negative and positive, according to the present embodiment of the present invention.

FIG. 6 is a table illustrating measured values of respective photometric parameters, and evaluations in a case where fibrin is mixed; and also illustrating measured values of photometric parameters and evaluations during a normal time, according to the present embodiment of the present invention.

FIG. 7 is a table illustrating photometric ranges and threshold values according to the present embodiment of the present invention.

EMBODIMENTS FOR CARRYING OUT THE INVENTION

Figure 1:
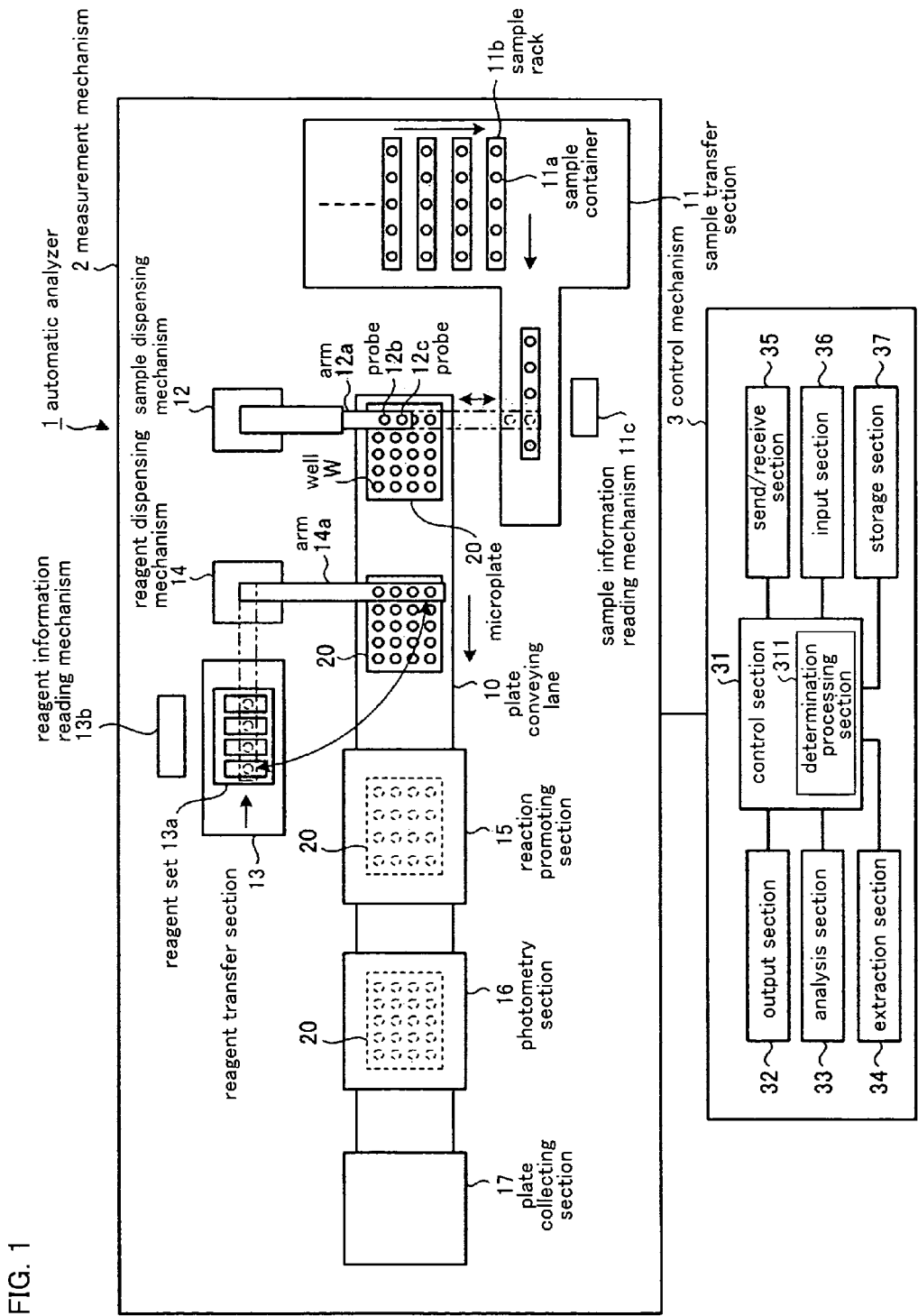
FIG. 1 is a schematic view illustrating a diagrammatic configuration of an automatic analyzer according to the present embodiment of the present invention.

Hereinafter, an embodiment of the present invention, an analyzer, will be described with reference to the attached figures. Note that the present invention is not limited to the present embodiment, and the same reference numerals are provided for identical parts in the descriptions of the figures.

FIG. 1 is a schematic view illustrating a configuration of an analyzer according to the present embodiment. As illustrated in FIG. 1, an automatic analyzer 1 according to the present embodiment comprises a measurement mechanism 2 for dispensing a sample to be analyzed and a reagent into predetermined wells W of a microplate 20 to measure a reaction caused in the wells W, and a control mechanism 3 for performing the controlling of the entire automatic analyzer 1 including the measurement mechanism 2 and for performing an analysis on a measurement result from the measurement mechanism 2. The conjunction of the two mechanisms allows the automatic analyzer 1 to perform immunological analysis of a plurality of samples automatically. The microplate 20 is a plate made of a transparent material, such as acrylic, and has a large number of apertures referred to as wells W that are opened on the surface of the microplate 20. Each of the wells W is a reaction container for housing a sample and a reagent for reaction with each other, and is an aperture with an inclined surface formed therein. The wells W are arranged in matrix on the surface of the microplate 20.

The measurement mechanism 2 broadly comprises: a plate conveying lane 10; a sample transfer section 11; a sample dispensing mechanism 12; a reagent transfer section 13; a reagent dispensing mechanism 14; a reaction promoting section 15; a photometry section 16; and a plate collecting section 17. Further, the control mechanism 3 comprises: a control section 31; an output section 32; an analysis section 33; an extraction section 34; a send/receive section 35; an input section 36; and a storage section 37. The respective sections that the measurement mechanism 2 and control mechanism 3 comprise are electrically connected with the control section 31. The sample dispensing mechanism and the reagent dispensing mechanism may be collectively referred to as a dispensing section. The plate conveying lane 10, the reaction promoting section 15, photometry section 16 and plate collecting section 17 as well as the microplate 20 may be understood as constituting a reaction section.

The plate conveying lane 10 conveys a microplate 20 to a predetermined position in order to dispense a sample and a reagent into each well W and to perform the promotion of a reaction and photometry on a liquid in the well W. Under the control of the control section 31 and by the driving of a drive mechanism (not shown), the plate conveying lane 10 conveys a microplate 20 in the left direction, for example, as illustrated by the arrow in FIG. 1.

The sample transfer section 11 comprises a plurality of sample racks 11b for retaining a plurality of sample containers 11a for housing samples, the sample racks 11b being transferred successively in the arrowed direction in the figure. The sample housed in each of the sample containers 11a is either a blood plasma, which is a supernatant obtained by adding an anticoagulant to a blood sample collected from a donor and centrifuging the blood, or a precipitate, which contains blood cell (red blood cell) separated by the centrifugation. The sample in each of the sample containers 11a transferred to a predetermined position on the sample transfer section 11 is dispensed by the sample dispensing mechanism 12 into a predetermined well W of a microplate 20 arranged on and conveyed by the plate conveying lane 10.

A recording medium is attached to a side surface portion of a sample container 11a. Sample information regarding a sample housed in a sample container 11a is recorded on the recording medium. The recording medium displays various types of encoded information, which is read optically. The sample information includes, for example, a name, sex and an age of a patient who donated the blood, menu of analysis, and the like.

A sample information reading mechanism 11c for optically reading the recording medium is provided for a corresponding portion of the sample transfer section 11. The sample information reading mechanism 11c emits infrared light or visible light onto the recording medium and processes reflected light off the recording medium to read the information of the recording medium. The sample information reading mechanism 11c may also obtain sample information from the recording medium by processing a captured image of the recording medium, and deciphering image information obtained by the processing of the captured image. The sample information reading mechanism 11c reads information on a recording medium attached to a sample container 11a when the sample container 11a passes in front of the sample information reading mechanism 11c.

The sample dispensing mechanism 12 comprises: an arm 12a with a probe 12b and a probe 12c for respectively suctioning and discharging a sample attached to a tip portion thereof; and a suction and discharge syringe or a suction and discharge mechanism using a piezoelectric element (not shown). The sample dispensing mechanism 12 suctions a sample through the probes 12b and 12c from a sample container 11a transferred to a predetermined position on the sample transfer section 11 described above, and moves the arm 12a in the top and bottom direction in the figure to dispense the sample by discharging it into each well W. Note that the probe 12b suctions and discharges a blood plasma in a sample container 11a and the probe 12c suctions and discharges blood cell particles in a sample container 11a.

The reagent transfer section 13 transfers a reagent set 13a to a reagent suction position for the reagent dispensing mechanism 14, where the reagent set 13a houses reagents dispensed in respective wells W on a microplate 20. In the reagent set 13a, predetermined amounts of required reagents are housed in accordance with various types of tests, and respective reagents included in one reagent set 13a may be for the purpose of dispensing a predetermined number of times, or may be for the purpose of dispensing one time. The reagent transfer section 13 collects a reagent set 13a which has gone through a predetermined number of times of dispensing processing, and transfers another reagent set 13a to be dispensed next to the reagent suction position.

A recording medium is attached to a side surface portion of a reagent set 13a. The recording medium displays various types of encoded information, which is read optically. A reagent reading mechanism 13b for optically reading the recording medium is provided for a corresponding portion of the reagent transfer section 13. The reagent reading mechanism 13b emits infrared light or visible light onto the recording medium and processes reflected light off the recording medium to read the information on the recording medium. The reagent reading mechanism 13b may also obtain information from the recording medium by processing a captured image of the recording medium, and deciphering image information obtained by the processing of the captured image.

The reagent dispensing mechanism 14 comprises an arm 14a with a probe for suctioning and discharging a reagent attached to a tip portion thereof. The arm 14a freely ascends and descends in a vertical direction and freely rotates around a vertical line passing through a base end section of the arm as the central axis. The reagent dispensing mechanism 14 comprises a suction and discharge syringe or a suction and discharge mechanism using a piezoelectric element (not shown). The reagent dispensing mechanism 14 suctions through each corresponding probe a reagent in a reagent set 13a moved to a predetermined position on the reagent transfer section 13, swivels the arm 14a counterclockwise in the figure, and dispenses each reagent by discharging it into each corresponding well W of a microplate 20 conveyed to a predetermined position on the plate conveying lane 10.

The reaction promoting section 15 promotes a reaction between a sample and a reagent dispensed in a microplate 20, causing an antigen-antibody reaction and forming an agglutination pattern on a bottom surface of each well W of the microplate 20. The reaction promoting section 15 stirs a sample and a reagent in a well W by vibrating the microplate 20, for example. Further, for example, the reaction promoting section 15 settles a microplate 20 for a predetermined period of time corresponding to the content of an analysis method so as to promote natural precipitation of blood cell particles, or the like. Further, for example, the reaction promoting section 15 applies a predetermined magnetic field to operate magnetic particles present in a well W.

The photometry section 16 photometrically detects an agglutination pattern formed by the reaction promoting section 15. The photometry section 16 is constituted of a CCD camera, for example, and captures an image of each well W of the microplate 20 from above and outputs image information of an image capturing the agglutination pattern formed in each well W. The photometry section 16 also comprises: a light emitting section for emitting a predetermined type of light onto each well W of a microplate 20; and a light receiving section for receiving light produced from a sample liquid in each well W, and the luminance of the light produced from the sample liquid may be output as a photometric result.

The plate collecting section 17 collects a microplate 20 which has gone through photometric processing by the photometry section 16. The collected microplate 20 is washed by a washing section (not shown) through suction and discharge of the mixed liquid of wells W and injection and suction of a washing liquid. The washed microplate 20 is reused. Note that the microplate 20 may be disposed of after the completion of one time measurement depending on the content of the test.

Next, the control mechanism 3 will be described. The control section 31 is constituted of a CPU and the like, and controls the processing by and operation of respective sections of the automatic analyzer 1. The control section 31 performs predetermined input and output controls on information input to and output from these elements, and performs predetermined information processing on the information. The control section 31 also comprises a determination processing section 311. The determination processing section 311 determines validity of an extracted measurement result on the basis of a photometric parameter of the measurement result.

The output section 32 is constituted of a display, a printer, a speaker and the like, and outputs various types of information including analysis information generated by the analysis section 33. The output section 32 also outputs image data extracted by the extraction section 34 on a screen.

The analysis section 33 analyzes an antigen-antibody reaction on the basis of a photometric result measured by the photometry section 16. In a case when the photometry section 16 outputs image information, the analysis section 33 processes the image information output by the photometry section 16 and obtains a photometric value in accordance with the luminance of the sample. The analysis section 33 also calculates a photometric parameter, using SPC (clearness of the edge of a image in the center), P (brightness of the periphery area), C (brightness of the center area), LIA (size of low brightness area) or the like, which are used for determining whether an agglutination reaction is positive or negative, and compares the photometric parameter with a threshold value of each of photometric parameters of SPC, P/C and LIA stored in the storage section 37. Note that the photometric parameters of SPC and P/C are obtained from a value between 0 and 99, and the photometric parameter of LIA is obtained from a value between 0 and 999. The numerical value of the calculated photometric parameter is compared with the threshold value of the photometric parameter and a determination can be made as + (positive), − (negative) or ? (undetermined; a case where the comparison result is in between positive and negative and it is not possible to determine which it is) for each of tests. Note that for the photometric parameter of P/C, P is divided by C and then the value multiplied by ten is used as the photometric parameter of P/C.

When there is a measurement result determined as negative by the analysis section 33, the extraction section 34 extracts a photometric parameter corresponding to the measurement result from the storage section 37 or a temporary storage area (not shown). The extracted photometric parameter is output to the determination processing section 311.

The send/receive section 35 has a function as an interface for sending and receiving information in accordance with a predetermined format via a communication network (not shown). The input section 36 is constituted of a keyboard, a mouse, a microphone or the like, and obtains various types of information necessary for analyzing a sample, instruction information of analysis operations, and the like from the outside. The send/receive section 35 also outputs an extraction menu to be displayed on a screen to the control section 31.

The storage section 37 is constituted of: a hard disk for magnetically storing information; and a memory for loading from the hard disk and electrically storing various programs associated with processing when the analyzer 1 executes such processing. The storage section 37 also stores test results as characteristic information and photometric parameters used for the test results, in association with one another, for each sample. Note that the storage section 37 may comprise an auxiliary memory unit capable of reading information stored on a storage medium, such as a CD-ROM, a DVD-ROM, a PC card or the like.

In the automatic analyzer 1 configured as described above, the sample dispensing mechanism 12 dispenses a sample from a sample container 11a, and the reagent dispensing mechanism 14 dispenses each reagent in the reagent set 13a, into a plurality of successively conveyed microplates 20; and then, the photometry section 16 captures a reaction image in a state in which the sample has reacted with the reagent; and the analysis section 33 does an analysis of the captured-image data, so that the analysis of the agglutination reaction of the sample and the like can be performed automatically.

Hereinafter, logical determinations of tests with regard to the ABO blood group and the Rho (D) blood group performed by the analysis section 33 will be described with reference to FIGS. 2 and 3. FIG. 2 is a table illustrating a combination of being negative (−) and positive (+) of respective reagents in relation to the ABO blood group, according to the present embodiment of the present invention. FIG. 3 is a table illustrating a combination of the Rho (D) blood group being negative and positive, according to the present embodiment of the present invention. The analysis section 33 combines the results of the respective reagents being negative and positive illustrated in FIGS. 2 and 3 to determine test results of the ABO blood group and the Rho (D) blood group as characteristic information of the sample. In the test results in the present embodiment, the ABO blood group is determined on the basis of the relationship illustrated in FIG. 2 and by combining agglutination reactions to the anti-A antibody (anti-A), anti-B antibody (anti-B), A blood cells (A cell) and B blood cell (B cell); and the Rho (D) blood group is determined on the basis of the relationship illustrated in FIG. 3 and by combining agglutination reactions to the anti-D antibody (anti-D) and the reference (Ref). Here, the determination of the ABO blood group can be made only with the anti-A antibody and the anti-B antibody.

Figures 4, 5:
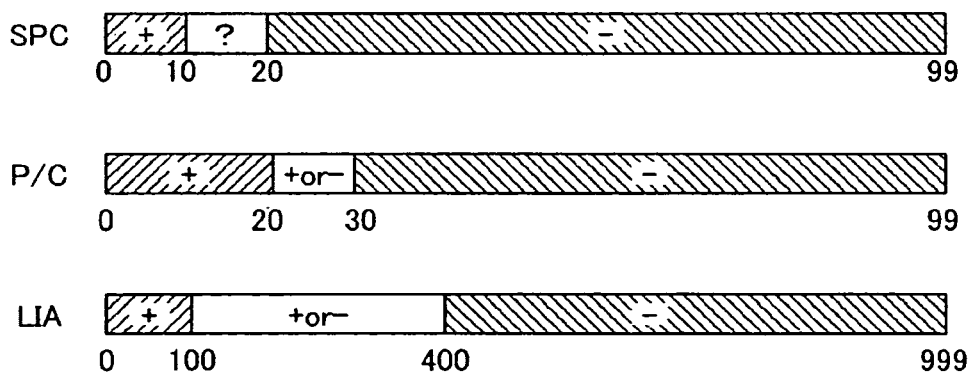
FIG. 4 is a table illustrating an example of threshold values of respective photometric parameters of the SPC, P/C and LIA according to the present embodiment of the present invention.
FIG. 5 is a graph illustrating the relationship between the threshold values of respective photometric parameters of the SPC, P/C and LIA illustrated in FIG. 4 and the evaluation of being negative and positive.

The determination of being negative and positive in the results of the reagents are derived from the comparison with the threshold values of respective photometric parameters of the SPC, P/C and LIA described above. FIG. 4 is a table illustrating an example of threshold values of respective photometric parameters of the SPC, P/C and LIA according to the present embodiment of the present invention. FIG. 5 is a graph illustrating the relationship between the threshold values of respective photometric parameters of the SPC, P/C and LIA illustrated in FIG. 4 and the determination of being negative and positive.

In an example of threshold values for qualitative determination illustrated in FIG. 4, the respective measured parameters of the SPC, P/C and LIA have a threshold value corresponding to a positive determination and a threshold value corresponding to a negative determination. The SPC is set to be 10 as a threshold value for the positive determination (Low), and the SPC is set to be 20 as a threshold value for the negative determination (High). The P/C is set to be 20 as a threshold value for the negative determination ((−) limit), and the P/C is set to be 30 as a threshold value for the positive determination ((+) limit). The LIA is set to be 100 as a threshold value for the negative determination ((−) limit) and the LIA is set to be 400 as a threshold value for the positive determination ((+) limit). The "ref" refers to a reference reagent; and a physiological salt solution not containing reactive components is mixed as a reagent with a sample to check a reaction image. The reference reagent always forms a negative reaction image, which can also be used for a comparison with measurement results of various tests.

In accordance with the setting of the threshold values for qualitative determination, on the basis of the calculated values of the photometric parameters, and with reference to the respective regions for determination illustrated in FIG. 5, the analysis section 33 judges whether or not the photometric parameter of each of respective reagents is negative. Specifically, with regard to the photometric parameter SPC, if the obtained value of the photometric parameter SPC is smaller than the threshold value for the positive determination (Low), i.e., 10, then the analysis section 33 judges the result to be positive. If the obtained value of the photometric parameter SPC is greater than the threshold value for the negative determination (High), i.e., 20, then the analysis section 33 judges the result to be negative. Moreover, if the value of the photometric parameter SPC is some value in between 10 to 20, then the analysis section 33 judges that the determination is not possible (FIG. 5: ?).

On the other hand, with regard to the photometric parameter P/C, if the obtained value of the photometric parameter P/C is smaller than the threshold value for the positive determination, i.e., 30, then the analysis section 33 judges the result to be positive. If the obtained value of the photometric parameter P/C is greater than the threshold value for the negative determination, i.e., 20, then the analysis section 33 judges the result to be negative. Moreover, if the value of the photometric parameter P/C is some value in between the two threshold values, i.e., in between 20 to 30, then the result can be determined to be either positive or negative (FIG. 5: + or −). In such a case, the reagent result is determined based on results of other photometric parameters. For the photometric parameter LIA, similar to the case with the P/C, the result of the photometric parameter LIA is judged to be positive if the value is smaller than the threshold value for the positive determination, i.e., 400; the result is judged to be negative if the value is greater than the threshold value for the negative determination, i.e., 100; and the result can be determined to be either positive or negative if the value of the photometric parameter LIA is some value in between the two threshold values, i.e., in between 100 to 400 (FIG. 5: + or −). In such a case, the reagent evaluation result is determined based on results of other photometric parameters. Note that the setting of the threshold values for qualitative determination of respective photometric parameters and the determination method of the reagent result are not limited to those described above.

After the analysis section 33 determines whether respective photometric parameters corresponding to the reagents are negative or positive, and if the determination result of the respective photometric parameters of the SPC, P/C and LIA are the same, the determination results of the photometric parameters are determined as the reagent result. Here, if even one of the determination results among the determination results of the SPC, P/C and LIA is different from the rest, the reagent evaluation result is determined to be undetermined. It is possible to set a priority for each of the respective photometric parameters, and to determine a reagent result using a determination result of one photometric parameter with a higher priority as a reagent result.

Using the reagent evaluation result obtained through the flow described above and in reference to the combinations illustrated in FIGS. 2 and 3, a result of evaluating each category is determined. Note that whether other reagents such as irregular antibodies are negative or positive can be determined in a similar flow.

Subsequently, the validity of the test result in a case where a foreign substance is mixed with a dispensed sample, e.g., a case where fibrin precipitates in a sample, will be described with reference to FIGS. 6, 7 and 8. Fibrin dissolves as fibrinogen into blood plasma, forms a fibrin polymer owing to the action of protease and calcium, and is associated with blood coagulation. For blood analysis, an anticoagulant is added in order to prevent the coagulation of blood due to fibrin; however, there have been cases where the precipitation of fibrin due to variation with time or a blood clot due to insufficient mixing of an anticoagulant occurs, and the precipitated fibrin or a blood clot is mixed into a reaction container to be captured as an image, causing an error evaluation for an examination result.

FIG. 6 is a table illustrating measured values of respective photometric parameters, and results in a case where fibrin is mixed; and also illustrating measured values of photometric parameters and results by normal dispensing, according to the present embodiment of the present invention. For the samples, the same samples were used and reaction processing and analysis processing were performed in a condition where one of the samples was mixed with fibrin (abnormal dispensing). As illustrated in FIG. 6, numerical values of the photometric parameters were calculated respectively with regard to the respective reagents, and the determination of being negative or positive was made on the basis of the numerical values.

Herein, with regard to the anti-A (anti-A antibody), the result of sample with suction of fibrin is different from the result by normal dispensing. Thus, type A sample is misdetermined as type O, which may cause an accident during a blood transfusion. This error occurs because an image of such a blood clot or precipitated fibrin is captured and the image of the blood clot or precipitated fibrin is erroneously recognized as a non-agglutinated image during the calculation of the respective photometric parameters, while the result is supposed to be determined as positive. In the present embodiment, such an erroneous result is recognized, and then the validity of the measurement result is confirmed.

The determination of the validity is made by calculating a photometric range illustrated in FIG. 6 and comparing it with the threshold values illustrated in FIG. 7. FIG. 7 is a table illustrating photometric ranges and threshold values according to the present embodiment of the present invention. Each of the photometric ranges is a value obtained by calculating the difference between the maximum value and the minimum value of numerical values of each photometric parameter of a reagent determined as negative among respective reagents used to analyze the same sample. For example, in a case of the LIA with abnormal dispensing (fibrin is suctioned), the maximum value is 869 of the anti-A and the minimum value is 390 of the anti-B, and the calculated difference, i.e., 479, is defined to be the photometric value range. Further, in a case of the LIA during normal dispensing, the maximum value is 689 of the anti-B and the minimum value is 679 of the ref, and the photometric value range is defined to be 10. By setting the threshold values illustrated in FIG. 7 for thus obtained photometric value ranges, whether or not respective parameters used for evaluation are reliable is determined, and whether or not the evaluation is valid is determined.

In FIG. 7, the photometric value ranges of the P/C and SPC are respectively 11 and 6 when fibrin is suctioned, but the P/C range and SPC range are both 1 when the sample is dispensed normally. Furthermore, when fibrin is suctioned, the LIA range is 479, which is a broad range among the respective reagents. But when the sample is dispensed normally, the range is 10, which is a small value. By providing a threshold value for such a difference between the photometric ranges, the validity of the test result is determined. Note that any threshold can be set, and a threshold value for the determination of invalidity can be changed in accordance with the categories of examination or the type of sample.

Next, the flow of the analysis processing described above will be described with reference to FIG. 8. FIG. 8 is a flowchart illustrating analysis processing performed by the automatic analyzer 1. If the control section 31 obtains captured-image data from the photometry section 16 (step S102), then the control section 31 instructs the analysis section 33 to calculate a photometric parameter from the obtained captured-image data (step S104); instructs the analysis section 33 to determine whether the respective reagents are negative or positive (step S106); and instructs the analysis section 33 to determine test results (characteristic information) based on the determined result of the step S106 (step S108).

After the determination of the test results (characteristic information), the control section 31 checks whether or not there is any reagent evaluation determined to be negative with regard to the reagents excluding the reference (step S110). Here, if there is any reagent that has been determined to be negative (step S110: Yes), the control section 31 instructs the extraction section 34 to extract a subject photometric parameter (step S112). After the extraction of the photometric parameter, the control section 31 outputs the extracted photometric parameter to the determination processing section 311, so that the photometric value range can be calculated (step S114).

After the calculation of the photometric range, the determination processing section 311 determines whether or not the photometric value range of each photometric parameter is less than the threshold value (steps S116 to S120). First, the determination processing section 311 determines whether or not the photometric value range (LIA range) of the photometric parameter LIA is less than the threshold value (step S116). Here, if the LIA range is less than the threshold value (step S116: Yes), then the determination processing section 311 moves on to the step S118 and determines whether or not the photometric value range (P/C range) of the photometric parameter P/C is less than the threshold value. If the P/C range is also less than the threshold value (step S118: Yes), the determination processing section 311 moves on to the step S120 and determines whether or not the photometric value range (SPC range) of the photometric parameter SPC is less than the threshold value. If the SPC range is less than the threshold value (step S120: Yes), then the determination processing section 311 determines that the test results are valid since the respective ranges of the photometric parameters are less than the respective threshold values, and the determination processing section 311 outputs information to the effect that the evaluations are valid to the control section 31. The control section 31 moves on to the step S124 owing to the input of the information to the effect that the evaluations are valid. At the step S124, if there is a measurement result of the next subject for analysis (step S124: Yes), then the control section 31 moves back to the step S102 to repeat the processing described above. If there is no measurement result (step S124: No), the operation ends.

On the other hand, if any of the photometric value ranges is greater than or equal to the corresponding threshold value at any of the steps S116 to S120 (steps S116, S118, S120: No), then the determination processing section 311 determines that the numerical value of the photometric parameter is abnormal, and adds evaluated result information to the effect that the numerical value is evaluated to be an abnormal value, to the test results (characteristic information) (step S122). Upon receiving the information to the effect that the evaluated result information has been added, the control section 31 moves on to the step S124.

Further, if there is no reagent evaluation determined to be negative at the step S110 (step S110: No), then the control section 31 moves on to the step S124.

Through the processing described above, whether or not the photometric parameters obtained from image data are valid is evaluated to determine the validity of the test results (characteristic information), thus making it possible to improve the reliability of obtained data.

Figure 8:
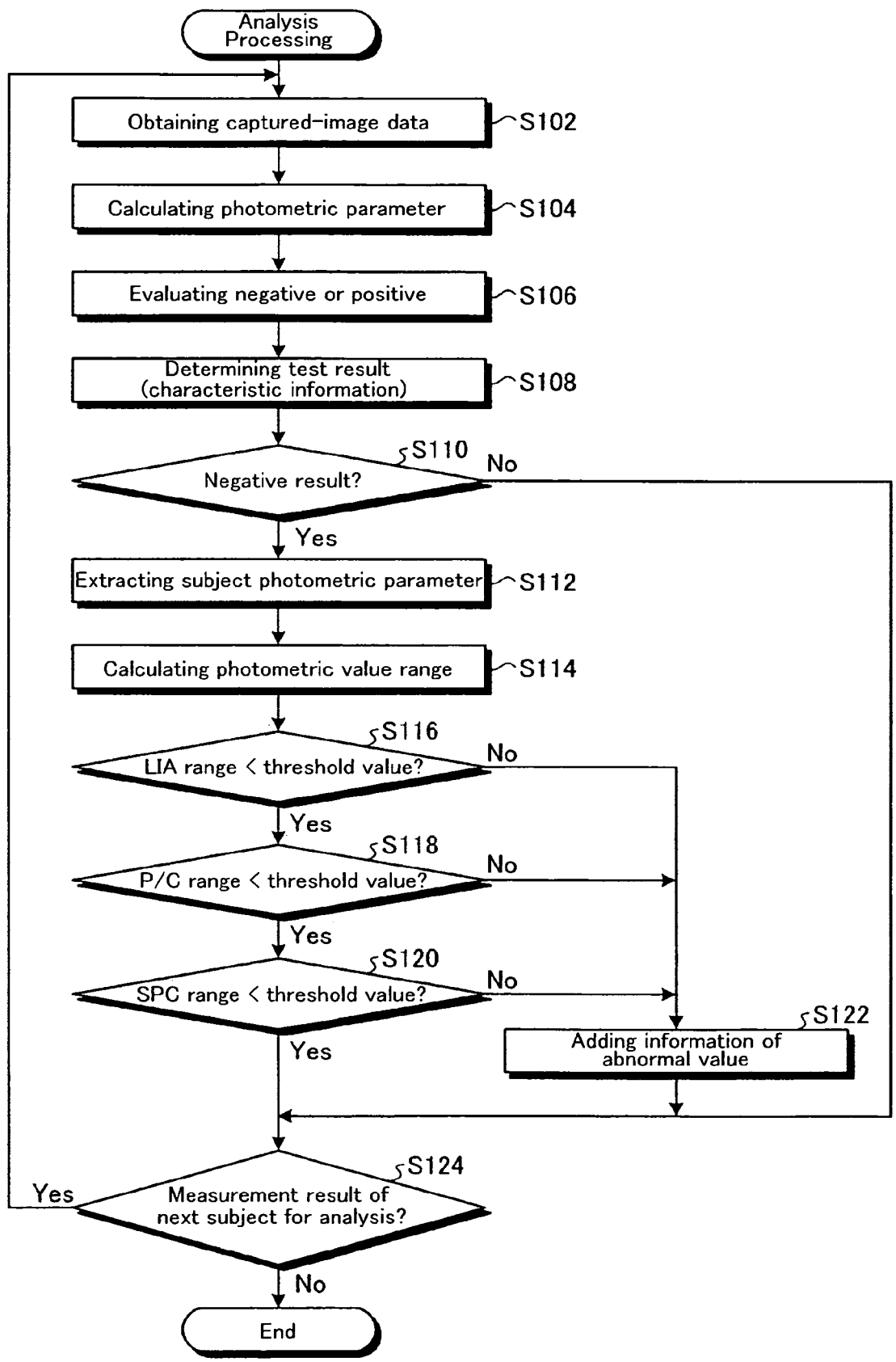
FIG. 8 is a flowchart illustrating analysis processing performed by the automatic analyzer 1.
Figure 9:
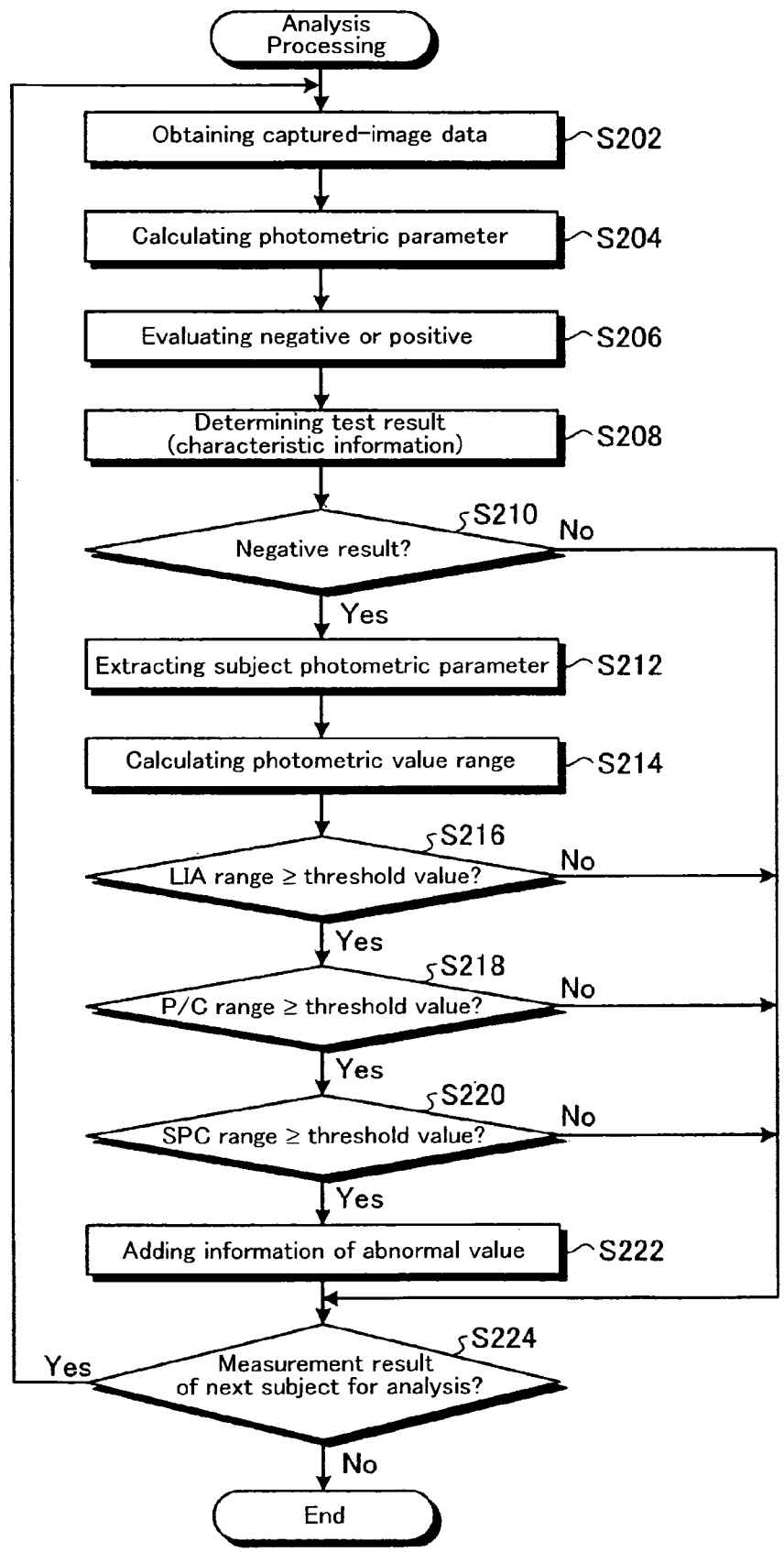
FIG. 9 is a flowchart illustrating a variation of analysis processing according to the present embodiment of the present invention.

It should be noted that while the three parameters LIA, P/C and SPC are determined to have an abnormal value if even one of the parameters exceeds the corresponding threshold value in the flowchart illustrated in FIG. 8, it is also possible to determine that the parameters have an abnormal value if all of the three parameters exceed the threshold values. FIG. 9 is a flowchart illustrating a variation of analysis processing according to the present embodiment of the present invention.

Similar to the flowchart illustrated in FIG. 8, if the control section 31 obtains captured-image data from the photometry section 16 (step S202), then the control section 31 instructs the analysis section 33 to calculate a photometric parameter from the obtained captured-image data (step S204); instructs the analysis section 33 to determine whether the respective reagents are negative or positive (step S206); and instructs the analysis section 33 to determine test results (characteristic information) based on the evaluation result of the step S206 (step S208).

After the determination of the test results (characteristic information), the control section 31 checks whether or not there is any reagent evaluation determined to be negative with regard to the reagents excluding the reference (step S210). Here, if there is any reagent that has been determined to be negative (step S210: Yes), the control section 31 instructs the extraction section 34 to extract a subject photometric parameter (step S212). After the extraction of the photometric parameter, the control section 31 outputs the extracted photometric parameter to the determination processing section 311, so that the photometric value range can be calculated (step S214).

After the calculation of the photometric range, the determination processing section 311 determines whether or not the photometric value range of each photometric parameter is greater than or equal to the threshold value (steps S216 to S220). First, the determination processing section 311 determines whether or not the photometric value range (LIA range) of the photometric parameter LIA is less than the threshold value (step S216). Here, if the LIA range is greater than or equal to the threshold value (step S216: Yes), then the determination processing section 311 moves on to the step S218 and determines whether or not the photometric value range (P/C range) of the photometric parameter P/C is greater than or equal to the threshold value. If the P/C range is also greater than or equal to the threshold value (step S218: Yes), the determination processing section 311 moves on to the step S220 and determines whether or not the photometric value range (SPC range) of the photometric parameter SPC is greater than or equal to the threshold value. If the SPC range is greater than or equal to the threshold value (step S220: Yes), then the determination processing section 311 determines that the photometric parameter has an abnormal value and the test results are invalid since the respective ranges of the photometric parameters are greater than or equal to the respective threshold values, and the determination processing section 311 adds, to test results (characteristic information), and outputs information to the effect that the photometric parameter has an abnormal value, to the control section 31 (step S222). Upon receiving the information to the effect that the test results are invalid, the control section 31 moves on to the step S224. At the step S224, if there is a measurement result of the next subject for analysis (step S224: Yes), then the control section 31 moves back to the step S202 to repeat the processing described above. If there is no measurement result (step S224: No), the operation ends.

On the other hand, if any of the photometric value ranges is less than the corresponding threshold value at any of the steps S216 to S220 (steps S216, S218, S220: No), then the determination processing section 311 determines that the numerical value of the photometric parameter is valid, and outputs information to the effect that the photometric parameter is valid to the control section 31. Upon receiving the information to the effect that the evaluated result information has been added, the control section 31 moves on to the step S224. Further, at the step S210, if there is no reagent evaluation determined to be negative at the step S210 (step S210: No), then the control section 31 moves on to the step S224.

Through the processing described above, a determination of such an abnormal value can be made when all the photometric value ranges of the respective photometric parameters exceed the respective thresholds.

In the present embodiment, while negative results are ascertained, except for the reference, at the steps S110 and S210, it is also possible to ascertain whether or not there is a plurality of negative results including the reference. Essentially, the result of the reference always turns out to be negative. Thus, if it is determined to be positive with regard to the reference, the cause is due to some other factors apart from the precipitation of fibrin or a blood clot. In that case, separate kinds of checking will be required.

Further, the order in which the photometric parameters are compared with thresholds can be in any order. The order can be changed to any order in accordance with the characteristics of the respective parameters with regard to the type of sample or reagents.

Here, the display of a result of test results, where the photometric parameter is evaluated to have an abnormal value and information to the effect that the photometric parameter has an abnormal value is added to the test results (characteristic information), may be made in such a manner that when the output section 32 displays the result of test results, the corresponding test results and/or reagent evaluations and/or photometric parameter portions are displayed with added shading; or the words and numerical values associated with the evaluation may be displayed with different colors.

Figure 10:
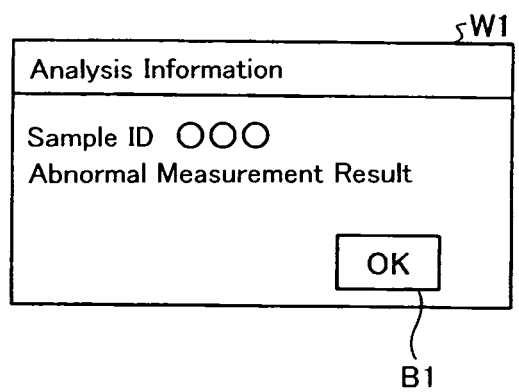
FIG. 10 is a diagram illustrating an example of a pop-up screen according to the present embodiment of the present invention.

Further, the output section 32 may also display a message when there is a photometric parameter which is evaluated to be abnormal. FIG. 10 is a diagram illustrating an example of a pop-up screen according to the present embodiment of the present invention. The output section 32 may display a sample ID as analysis information and a message to the effect that a measurement result is abnormal, on a monitor or the like, such as a pop-up screen W1 illustrated in FIG. 10.

For the timing of the displaying, it may take place when the result is determined as abnormal, or when an operator checks the result. It is also possible to set the pop-up screen W1 to be closed when the operator checks the message and presses an OK button B1, or it is also possible to set a screen for checking a measurement result to be displayed automatically when the OK button B1 is pressed.

The automatic analyzer according to the embodiment described above allows a measurement result that is misdetermined due to contamination of a foreign substance to be extracted appropriately and checked. Besides the case with fibrin, the automatic analyzer is capable of coping with such a case when a foreign substance contaminates a sample (in a captured image). According to the analysis processing of the present embodiment, since the determination as to whether or not a measurement result is valid can be made on the basis of the change in the captured image, the comparison of numerical values of photometric parameters allows an invalid measurement result to be extracted appropriately.

Here, with regard to the flowcharts in FIGS. 8 and 9, as to the photometric parameters that are compared with threshold values, it is possible to compare only a photometric parameter in which the measured value changes most significantly due to contamination of a foreign substance, e.g., the photometric value range of LIA, with a threshold. It is also possible to compare respective photometric value ranges of two optionally selected photometric parameters, e.g., LIA and P/C, with threshold values. The photometric parameters used in the present invention are optionally selectable in accordance with the characteristics of reagents or properties of samples.

A control program for controlling the processing executed by the automatic analyzer 1 is installed on the storage section 37 of the control mechanism 3 illustrated in FIG. 1. In general, installment of such a control program on a memory of a computer allows the computer to function as a part or all of the control mechanism 3 (FIG. 1). Such a control program may be installed on a memory prior to the shipping of the computer, or may be installed on a memory after the shipping of the computer. The program may be installed on a memory of the computer by reading the program recorded on a recording medium, or the program that is downloaded via a network, such as the Internet, may be installed on a memory. As to the computer, any type of computer can be used.

Once the control program is installed on a computer, the computer will function as a part or all of the control mechanism 3 (FIG. 1). In this case, the control mechanism 3 (FIG. 1) in operation means that a control method corresponding to the installed control program is being executed. This is because the control method corresponds to the operation method of the control mechanism.

As described above, the present invention is exemplified by the use of its preferred embodiment. However, the present invention should not be interpreted solely based on the embodiment described above. It is understood that the scope of the present invention should be interpreted solely based on the claims. It is also understood that those skilled in the art can implement equivalent scope of technology, based on the description of the present invention and common knowledge from the description of the detailed preferred embodiment of the present invention. Furthermore, it is understood that any patent, any patent application and any references cited in the present specification should be incorporated by reference in the present specification in the same manner as the contents are specifically described therein.

The present application claims priority to Japanese Patent Application No. 2009-269039, and it is understood that the entire contents of which are incorporated by reference herein as a part constituting the present specification in the same manner as the contents are specifically described in the present specification.

INDUSTRIAL APPLICABILITY

As described above, the automatic analyzer according to the present invention is useful for extracting a misdetermined measurement result, and is particularly suitable for analysis processing which is made based on an image.

REFERENCE SIGNS LIST 1 automatic analyzer
2 measurement mechanism
3 control mechanism
10 plate conveying lane
11 sample transfer section
11a sample container
11b sample rack
11c sample information reading mechanism
12 sample dispensing mechanism
12a, 14a arm
12b, 12c probe
13 reagent transfer section
13a reagent set
13b reagent reading mechanism
14 reagent dispensing mechanism
15 reaction promoting section
16 photometry section
17 plate collecting section
20 microplate
31 control section
311 determination processing section
32 output section
33 analysis section
34 extraction section
35 send/receive section
36 input section
37 storage section

The invention claimed is:

1. An automatic analyzer for analyzing a blood sample using a plurality of reagents, comprising:
   a container for containing a blood sample;
   a plurality of containers for containing a plurality of reagents; a dispensing section for dispensing the sample and the plurality of reagents;
   a reaction section including a substrate having a plurality of reaction containers, each container for allowing the blood sample to react with one of the plurality of reagents therein;
   a photometry section for capturing an image of the inside of each of the reaction containers;
   a control section;
   an analysis section coupled to the control section, the analysis section for analyzing the sample on the basis of whether or not reactions have occurred inside the reaction containers: and,
   a storage section coupled to the control section and comprising a control program, the control program for implementing processing executed by the automatic analyzer,
   the control section configured to:
   analyze a plurality of images of the inside of the plurality of reaction containers captured by the photometry section,
   wherein the analysis comprises calculating a measurement result comprising a numerical value of a photometric parameter of each of the images in accordance with the luminance of the sample, wherein the numerical value of the photometric parameter is compared with a threshold value to determine whether an agglutination reaction is positive or negative, and analyzing characteristic information of the sample;
   wherein when no agglutination reaction has occurred in the reaction containers being defined as negative,
   calculate a difference between a maximum value and a minimum value of the photometric parameter for the different reagents used to analyze the same sample when the agglutination reactions for the different reagents are negative, determine whether or not the measurement result is valid by comparing the calculated difference with a predetermined threshold of the photometric parameter, and add a validity result of the determination to characteristic information of the corresponding sample.

2. The automatic analyzer according to claim 1, wherein the control section is configured to calculate a plurality of photometric parameters for each of the images wherein:

at least two of the photometric parameters are selected from the group consisting of P/C, SPC and LIA;

the control section is configured to determine that the measurement result is invalid if the difference of at least one of the photometric parameters is outside a predetermined range; and wherein P/C stands for peripheral/center, SPC stands for sharpness between peripheral and center, and LIA stands for low intensity area.

3. The automatic analyzer according to claim 2, wherein one of reagents used is a reference reagent that always indicates negative.

4. The automatic analyzer according to claim 3, wherein the control section is configured to exclude the reference reagent from the different reagents.

5. The automatic analyzer according to claim 1, wherein the control section is configured to calculate a plurality of photometric parameters for each of the images wherein:

at least one of the photometric parameters is selected from the group consisting of P/C, SPC and LIA;

the control section is configured to determine that the measurement result is invalid if the difference of all of the photometric parameters is outside a predetermined range; and wherein P/C stands for peripheral/center, SPC stands for sharpness between peripheral and center, and LIA stands for low intensity area.

6. The automatic analyzer according to claim 5, wherein one of reagents used is a reference reagent that always indicates negative.

7. The automatic analyzer according to claim 6, wherein the control section is configured to exclude the reference reagent from the different reagents.

8. The automatic analyzer according to claim 5, wherein the control section is configured to calculate the difference between a maximum value and a minimum value of LIA for the different reagents, wherein LIA stands for low intensity area.

9. The automatic analyzer according to claim 1, wherein one of reagents used is a reference reagent that always indicates negative.

10. The automatic analyzer according to claim 9, wherein the control section is configured to exclude the reference reagent from the different reagents.

11. The automatic analyzer according to claim 1, further comprising an output section for outputting information to the effect that the measurement result is invalid if the measurement result is determined to be invalid by the control section.

12. The automatic analyzer according to claim 1, wherein the control section is configured to analyze the characteristic information of the sample by a combination of the agglutination reactions of the respective reagents being negative or positive.

13. The automatic analyzer according to claim 1, wherein the plurality of reaction containers are arranged in matrix on a surface of a microplate.

* * * * *